United States Patent
Hart et al.

(10) Patent No.: US 7,452,503 B2
(45) Date of Patent: Nov. 18, 2008

(54) KINETIC AIR DISPENSER

(76) Inventors: Gerald Leslie Hart, deceased, late of Surbiton, Surrey (GB); by Susan Hart, legal representative, 38 Villers Avenue, Surbiton, Surrey, KT5 8BD (GB); Colin William Brown, 5 Clandon Avenue, Egham, Surrey, TW20 8LP (GB); Guy Edward Naish, 123 Coopers Green, Bicester, Oxfordshire, OX26 4US (GB); Kishen Gohil, 21 Consfield Avenue, KT3 6HB, New Malden, Surrey (GB)

( * ) Notice: Subject to any disclaimer, the term of this patent is extended or adjusted under 35 U.S.C. 154(b) by 835 days.

(21) Appl. No.: 10/766,426

(22) Filed: Jan. 27, 2004

(65) Prior Publication Data

US 2004/0250962 A1 Dec. 16, 2004

(51) Int. Cl.
*A61L 9/12* (2006.01)
(52) U.S. Cl. .......................... 422/5; 422/124

(58) Field of Classification Search ....................... None
See application file for complete search history.

(56) References Cited

U.S. PATENT DOCUMENTS 4,016,439 A * 4/1977 Sheridan ....................... 310/39
2002/0197188 A1* 12/2002 Lua ............................. 422/124

FOREIGN PATENT DOCUMENTS

WO WO 0166158 A1 * 9/2001

* cited by examiner

*Primary Examiner*—Elizabeth L McKane

(57) ABSTRACT

An apparatus useful for disseminating volatile liquid such as fragrance into an atmosphere from an evaporating surface adapted to oscillate in the atmosphere. Oscillation is caused and maintained by means of two magnets, one a permanent magnet, the other an electromagnet, one of which is attached to the evaporating surface. The electromagnet is caused to repel the permanent magnet at such points in the oscillation that the oscillation is maintained.

8 Claims, 2 Drawing Sheets

KINETIC AIR DISPENSER

This invention relates to a an apparatus or device for dissemination of volatile liquid into an atmosphere, e.g., an air treatment material which uses kinetic motion to achieve this dissemination.

The invention provides an apparatus adapted to disseminate volatile liquid into an atmosphere, dissemination being effected by an evaporation surface that is caused to oscillate in the atmosphere with respect to a stationary support by means of the repulsion of a pair of magnets, one attached to the evaporation surface, the other to the support, one being a permanent magnet, the other an electromagnet, the electromagnet being actuated or operating in such a manner as to maintain the oscillation.

The invention further provides a method of disseminating a volatile liquid into an atmosphere, comprising causing an evaporation surface that is supplied with liquid to oscillate in the atmosphere, the oscillation being maintained by means of a pair of magnets, one a permanent magnet, the other an electromagnet, one of these being attached to the evaporation surface, the electromagnet being caused to repel the permanent magnet at a suitable point in the oscillation such that the oscillation is maintained.

By "oscillate" is meant a pendulum-like, back-and-forth motion in a plane perpendicular to the axis of oscillation, usually a vertical plane.

By "attached to the evaporation surface" is meant that the magnet is attached or otherwise mounted to the surface directly or indirectly, or alternately mounted in or upon part of the oscillating portion or body portion in such a manner that the two magnets may be brought into sufficiently close proximity that magnetic repulsion can cause the continuation of oscillation when the device operates.

The use of magnets to create such oscillation is well known and has been employed, for example, in "executive toys" or "kinetic art". However, the concept that such motion may be utilised in a practical application, rather than for purely decorative or amusement purposes, is new.

In a typical apparatus (device) according to the invention, there is present a stationary support in which there is included an electromagnet equipped with a power source. (It is possible, although less preferred, that the electromagnet be attached to the evaporating surface, but further description of the invention will be restricted to the variant with the electromagnet in the stationary support). This may be any suitable power source, for example, mains electricity, battery or solar cells. From the stationary support extend at least one, preferably two support arms, which pivotally support the oscillating portion of the device by means of at least one, preferably two coaxial pivot arms extending therefrom, thus defining the axis of oscillation. The oscillating portion comprises an upright body portion perpendicular to the axis of oscillation when it is mounted on the support and which extends both above and below the axis of oscillation. At or near the lowest region of the oscillating portion of the device there is provided a permanent magnet which, when the electromagnet is deactivated, is held just clear of the stationary support. The electromagnet in the stationary support is situated just below this point. That part of the body portion that extends above the axis of oscillation is preferably dimensioned so as to partially counterbalance the permanent magnet. Most desirably however, the body portion containing the permanent magnet or the oscillating portion containing the permanent magnet should always be heavier, so that it will tend to hang lower, under the influence of gravity. The body portion may be a removable unit which may be removably affixed or mounted to the oscillating portion which cradles the body portion; alternately the oscillating portion is the same as the body portion of the device. According to one preferred embodiment the permanent magnet is mounted in or upon part of the oscillating portion. According to a different preferred embodiment the permanent magnet is mounted in or upon the body portion.

In use, the electromagnet is activated and the oscillating portion manually pushed to start its oscillation. Such oscillation is preferably pendular, with the oscillating portion swinging in a vertical plane perpendicular to the axis of oscillation. Of course, motion in other directions is also contemplated although less preferred, including in a horizontal direction or other orientation. The magnets present in the device are set such that, when power is applied to the electromagnet, its polarity will oppose that of the permanent magnet and repel it; this repulsion causes the oscillating portion to be given a boost each time the magnet in the oscillating portion passes the electromagnet, thus maintaining the oscillatory motion of the device.

The power supplied to the electromagnet may be regulated by any suitable electromagnet control means. One such means which is particularly preferred is by the use of a timer or timer circuit. On activation and deflection, power is applied to the electromagnet for sufficient time to push the oscillating portion of the device to full deflection away from the electromagnet. At this point, the power to the electromagnet is cut. As the oscillating portion continues to oscillate, it loses energy on each swing and thus the angle of deflection is less each time, however these losses are compensated for by the action of the permanent magnet. The power to the permanent magnet may be controlled by a timer which is set to activate just above the minimum deflection point, e.g., when the permanent magnet and the electromagnet overlap or in near proximity to one another. This is determined by the minimum deflection from vertical in which the oscillating portion needs to be moved (with power on) to allow the electromagnet to push the oscillating portion to full deflection. The power is then continued until such time as the oscillating portion reaches full deflection again. This mechanism allows for conservation of battery power and the extension of the overall operational period of the apparatus with a single set of batteries. Alternately, the electromagnet control means may, instead of a timer or timer circuit utilize a power control circuit which varies the power output of the electromagnet in order to impel a suitable deflection of the oscillating portion from the electromagnet. In a further alternative power supply to the electromagnet may be regulated by a switch circuit which includes one or more electrical contacts which function as switches are mounted on either the support arm(s) or the coaxial pivot arm(s) or both, such that during oscillation of the oscillating portion power is supplied to the electromagnet when the permanent magnet and the electromagnet overlap or in near proximity to one another, which would then energize the electromagnet and deflect the oscillating portion. Such an arrangement could be achieved by providing a small area of an electrically conductive material (e.g., metal foil) on part of the coaxial pivot arm(s) which would bridge two spaced apart electrical leads within the support arm(s) on which the coaxial pivot arm(s) are mounted, such that when the permanent magnet and the electromagnet overlap or in near proximity to one another the said small area bridges the electrical leads, an electrical circuit is closed and the electromagnet is energized. When the oscillating portion further oscillates away from this position, the electrically conductive material (e.g., metal foil) on part of the coaxial pivot arm(s) disengages one or both of the electrical leads and thereby breaks the electrical circuit, until the oscillating portion returns from the apogee of its swing and returns.

The evaporating surface may be any suitable evaporating surface. For example, it may be a porous wick of the type well known in existing air fresheners. This wick conveys liquid from a reservoir within the oscillating body portion to an interface with the atmosphere, the oscillation of which causes the liquid to evaporate into the atmosphere. Preferably, this wick should terminate in a relatively large evaporation surface. This may be provided, for example, by making the wick with a flattened end, or by providing a standard cylindrical wick with a flat evaporating surface. In the latter case, the cylindrical wick is a primary wick and the flat surface a secondary wick. The secondary wick may be of any suitable configuration, and it may be solid, porous or perforated to any desired degree. In a practical embodiment, either or both of the primary and secondary wicks would be enclosed by any suitable means to prevent their being touched. In all embodiments the evaporating surface is in fluid communication with the contents of the reservoir.

A reservoir is situated within the oscillating portion or within the body portion. It is preferably located such that it is close to the axis of oscillation, so that the gradual emptying of the reservoir would have a reduced effect on the period of oscillation. The reservoir is preferably a detachable reservoir, so that the apparatus may easily be replenished.

If desired, evaporation from the evaporation surface may by augmented by forced ventilation from a fan or other suitable means.

In a preferred embodiment, the reservoir and one or both of the primary and secondary wicks are supplied as a single unit, so that the apparatus can easily and quickly be refilled, by removing an empty unit and replacing it with a full one. In another preferred variant of this embodiment, the secondary wick comprising the evaporation surface remains on the apparatus and the reservoir and primary wick are supplied as a single refill, sealed by any suitable means, such as a screw cap or a foil. The refill may then be fitted into the oscillating body by any suitable means, such as screwing or snap-fitting into place.

In accordance with one preferred embodiment, the body portion comprises a reservoir and wick as a single unit, which body portion is removable from the oscillating portion of the device.

The volatile liquid may be any liquid air treatment material whose presence in an atmosphere is desired. Typical examples include fragrances, disinfectants, insecticides, fungicides and medicaments. An especially useful application of the apparatus of the invention is as an air freshener in homes or hotel rooms.

The invention is now further described with reference to the accompanying drawings, which depict a preferred embodiment, and are not intended to be limiting in any way on the scope of the invention.

Figure 1:
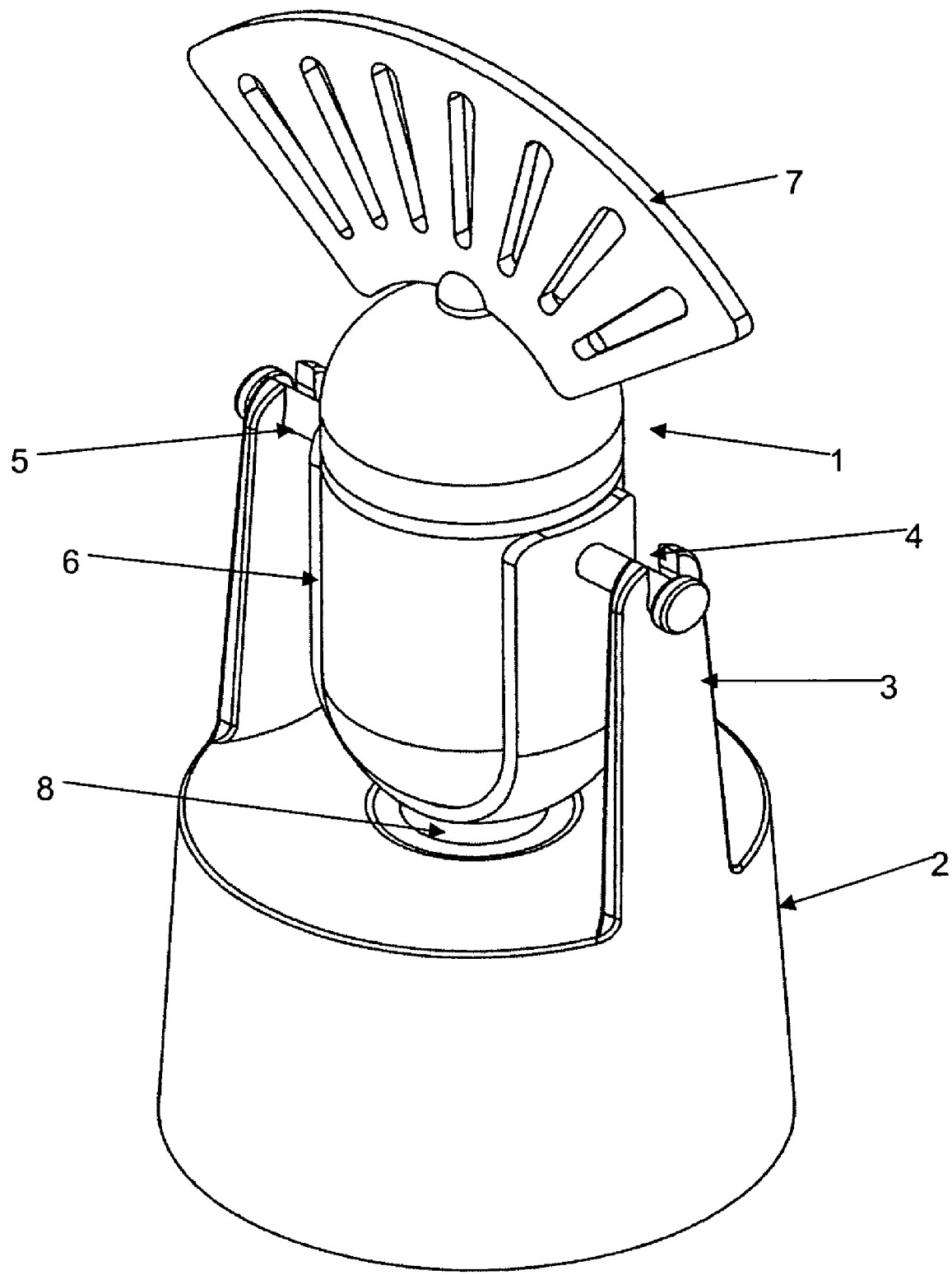
FIG. 1 shows a perspective view of an apparatus according to the invention.
Figure 2:
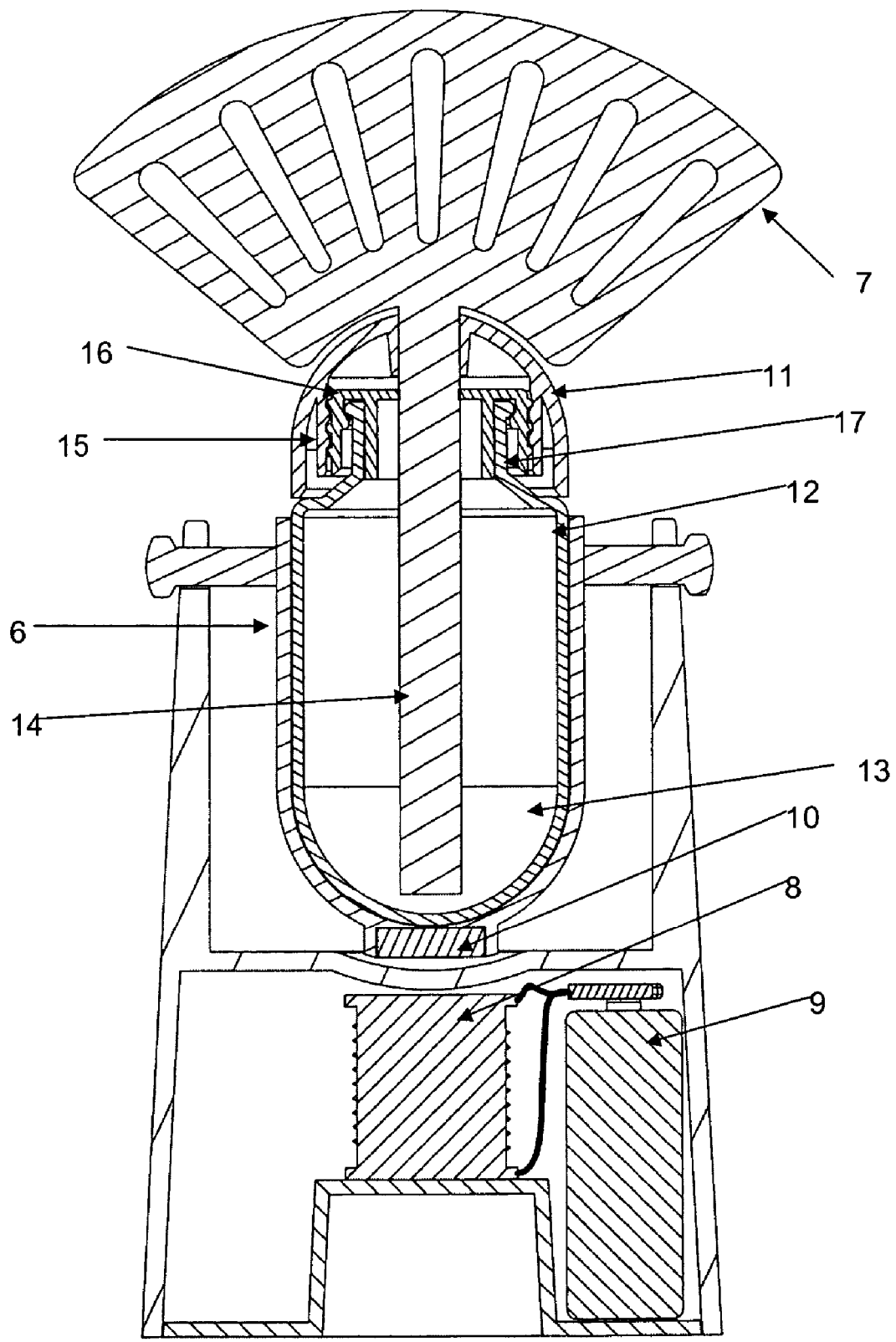
FIG. 2 shows a longitudinal cross-section through the apparatus of FIG. 1.

A body portion generally indicated as 1, is pivotally mounted on a base 2 by means of two raised arms 3 with cutouts 4 adapted to receive horizontal axles 5 of a cradle 6 into which the body portion 1 tightly fits. From the top of the body portion 1 extends a vane-like wick 7. Beneath the bottom of the cradle in the base is an electromagnet 8, which receives power from a battery 9 mounted within the base. Into the bottom of the cradle 6 is fixed a permanent magnet 10. The dimensions of the various parts are selected such that the cradle with the body portion can swing freely, with the permanent magnet 10 narrowly clearing the top of the base where the electromagnet 8 is housed, such that the switching on of the electromagnet will cause the permanent magnet to be repelled.

The body portion 1 consists of two parts, a cap 11 and a reservoir 12 containing the liquid to be evaporated 13. From the vane-like wick 7 there extends downwards into the liquid a cylindrical wick 14 that is integral with the vane-like wick 7. The liquid rises up this cylindrical wick 14 to the vane-like wick 7.

The cap 11 and the reservoir 12 are held together by cooperating screw threads 15, one thread being provided in the interior of the cap 11 and the other provided in the exterior of a closure 16 that is snap-fitted on to a neck 17 of the reservoir 12. The cylindrical wick 14 passes through orifices in the closure 16 and the cap 11 and is a tight fit within them.

In operation, the body portion 1 is manually started oscillating and the electromagnet 8 is actuated. Timing circuitry (not shown) switches the electromagnet on and off such that a repelling magnetic force is applied to the permanent magnet as it passes over the electromagnet. The oscillation is thus kept going.

The skilled person will realise that there are many variations of the apparatus of this invention that can be produced and which fall within the scope of this invention. For example, there are many possibilities of construction of the body portion and the wick, allowing for the possibility of different refills and different wicks (such as, as previously mentioned, separate primary and secondary wicks).

The invention claimed is:

1. An apparatus adapted to disseminate volatile liquid into an atmosphere, comprising:
   a stationary support with at least one stationary support arm extending from the stationary support,
   an electromagnet connected to a power source,
   an electromagnet control means;
   an oscillating portion comprising a reservoir and an evaporating surface, the reservoir containing an air treatment material in fluid communication with the evaporating surface, the oscillation portion additionally comprising at least one pivot arm, which pivotally supports the oscillating portion on the stationary support arm, and a permanent ma net disposed at or near the lowest region of the oscillating portion; and
   wherein the electromagnet control means maintains oscillatory motion of the oscillating portion with respect to the stationary support and dissemination of the air treatment material to the atmosphere through the oscillating evaporating surface.

2. The apparatus according to claim 1, wherein the oscillating portion includes a body portion.

3. The apparatus according to claim 1, wherein the oscillating portion is a body portion.

4. The apparatus according to claim 1, wherein the electromagnet control includes a timer or timer circuit.

5. The apparatus according to claim 1, wherein the electromagnet control means is a power control circuit.

6. The apparatus according to claim 1, wherein the electromagnetic control means is a switch circuit.

7. The apparatus according to claim 1, which comprises a primary wick and a secondary wick.

8. A method of disseminating a volatile liquid into an atmosphere, comprising the steps of
   providing an apparatus according to claim 1, operating the device and thereby causing the oscillation of the oscillating portion of the device, the oscillation being maintained by means of a pair of magnets of the device, to cause an evaporation surface that is supplied with liquid to oscillate in the atmosphere.

* * * * *